(12) United States Patent
Lang et al.

(10) Patent No.: US 6,383,231 B1
(45) Date of Patent: May 7, 2002

(54) MIXTURE FOR THE OXIDATION TINTING OF KERATIN FIBRES CONTAINING A LACCASE AND TINTING METHOD USING SAID MIXTURE

(75) Inventors: Gérard Lang, Saint Prix; Jean Cotteret, Verneuil/Seine, both of (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/600,127

(22) PCT Filed: Jan. 12, 1999

(86) PCT No.: PCT/FR99/00039

§ 371 Date: Sep. 5, 2000

§ 102(e) Date: Sep. 5, 2000

(87) PCT Pub. No.: WO99/36046

PCT Pub. Date: Jul. 22, 1999

(30) Foreign Application Priority Data

Jan. 13, 1998 (FR) ............................................. 98 00253

(51) Int. Cl.⁷ .......................... A61K 7/13; C09B 67/00; D06P 5/12
(52) U.S. Cl. ....................... 8/405; 8/401; 8/406; 8/408; 8/455; 8/504; 8/908
(58) Field of Search ........................... 8/401, 408, 455, 8/504, 908, 405

(56) References Cited

U.S. PATENT DOCUMENTS

| | | |
|---|---|---|
| 3,251,742 A | 5/1966 | Soloway |
| 3,907,799 A | 9/1975 | O'Brien et al. |
| 4,003,699 A | 1/1977 | Rose et al. |
| 4,823,985 A | 4/1989 | Grollier et al. |
| 5,001,114 A | 3/1991 | McDaniel, Jr. |
| 5,009,880 A * | 4/1991 | Grollier et al. ............... 424/47 |
| 5,061,289 A | 10/1991 | Clausen et al. |
| 5,380,340 A | 1/1995 | Neunhoeffer et al. |
| 5,667,531 A * | 9/1997 | Yaver et al. .................... 8/401 |
| 5,766,576 A | 6/1998 | Löwe et al. |
| 5,776,443 A * | 7/1998 | Vinski et al. ............. 424/70.12 |
| 5,948,121 A * | 9/1999 | Aaslyng et al. ................ 8/401 |
| 5,981,243 A * | 11/1999 | Berka et al. ................. 435/189 |

FOREIGN PATENT DOCUMENTS

| | | |
|---|---|---|
| DE | 23 59 399 | 6/1975 |
| DE | 38 43 892 | 6/1990 |
| DE | 39 18 135 | 12/1990 |
| DE | 40 21 760 | 1/1992 |
| DE | 41 33 957 | 4/1993 |
| DE | 42 39 390 | 5/1994 |
| DE | 43 36 803 | 5/1995 |
| DE | 43 37 035 | 5/1995 |
| DE | 44 43 645 | 6/1996 |
| DE | 195 43 988 | 5/1997 |
| EP | 0 504 005 | 9/1992 |
| EP | 0 628 559 | 12/1994 |
| FR | 2 112 549 | 6/1972 |
| FR | 2 586 913 | 3/1987 |
| FR | 2 694 018 | 1/1994 |
| FR | 2 733 749 | 11/1996 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 94/27573 | 12/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/01644 | 1/1996 |
| WO | WO 96/15765 | 5/1996 |
| WO | WO 97/19998 | 6/1997 |
| WO | WO 97/19999 | 6/1997 |

OTHER PUBLICATIONS

Vishnu J. Ram et al., "Synthesis of bioisosteric pyrazolo [1–5–a]pyrimidines as leishmanicides", Indian Journal of Chemistry, vol. 34B, Jun. 1995, pp. 514–520.

Robert H. Springer et al., "Synthesis and Enzymic Activity of 6–Carbethoxy– and 6–Ethoxy–3,7–disubstituted–pyrazolo[1,5–a]pyrimidines and Related Derivatives as Adenosine Cyclic 3',5'–Phosphate Phosphodiesterase Inhibitors", J. Med. Chem., vol. 25, 1982, pp. 235–242.

Thomas Novinson et al., "Synthesis and Antifungal Properties of Certain 7–Alkylaminopyrazolo[1,5–a]pyrimidines", J. Med. Chem. vol. 20, No. 2, 1977, pp. 296–299.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine With β–Aminocrotonitrile: Synthesis of 2,7–Dimethyl–5–Aminopyrazolo[1,5–a]pyrimidine", Heterocycles, vol. 6, No. 9,10, 1977, pp. 1355–1360.

(List continued on next page.)

*Primary Examiner*—Blaine Copenheaver
*Assistant Examiner*—Thai Vo
(74) *Attorney, Agent, or Firm*—Finnegan, Henderson, Farabow, Garrett & Dunner, L.L.P.

(57) ABSTRACT

The invention relates to a ready-to-use mixture for tinting keratin fibres, especially human keratin fibres such as hair, comprising in a support material suitable for keratin materials: a) at least one laccase-type enzyme; at least one anionic surface-active agent selected from the group made up of the acylisethionates, acyltaurates, sulfosuccinates having a special structure, acylsarcosinates having a special structure, acyl glutamates, polyoxyalkylenated carboxylic acid ethers and their salts, fatty glucamide sulfates, alkyl galactoside uronates, anionic derivatives of alkyl polyglucoside, and mixtures thereof; and (c) at least one oxidation tint. The invention also relates to the hair tinting methods using the above mixture.

40 Claims, No Drawings

OTHER PUBLICATIONS

Koji Saito et al., "The Reaction of Ethyl Ethoxymethyl-enecyanoacetate with Its Hydrazino Derivatives", Bulletin of the Chemical Society of Japan, vol. 47, No. 2, 1974, pp. 476–480.

Ermitas Alcalde, "Etude de la réaction du β–aminocrotoni-trile et du α–formyl phénylacétonitrile avec l'hydrazine: synthése d'amino–7 pyrazolo[1,5–a]pyrimidines", Journal of Heterocyclic Chemistry, vol. 11, No. 3, Jun. 1974, pp. 423–429.

Martin M. Rieger, "Surfactant Chemistry and Classification", Surfactants in Cosmetics, Second Edition, 1997, pp. 1–28.

English language Derwent Abstract of DE 39 18 135.
English language Derwent Abstract of DE 40 21 760.
English language Derwent Abstract of DE 42 39 390.
English language Derwent Abstract of DE 43 36 803.
English language Derwent Abstract of DE 43 37 035.
English language Derwent Abstract of DE 44 43 645.
English language Derwent Abstract of EP 0 504 005.
English language Derwent Abstract of FR 2 112 549.
English language Derwent Abstract of FR 2 694 018.
English language Derwent Abstract of FR 2 733 749.
English language Derwent Abstract of JP 2–19576.
English language Derwent Abstract of JP 5–163124.

* cited by examiner

MIXTURE FOR THE OXIDATION TINTING OF KERATIN FIBRES CONTAINING A LACCASE AND TINTING METHOD USING SAID MIXTURE

The present invention relates to a dyeing composition for keratinous fibres, comprising at least one enzyme of the laccase type, at least one particular anionic surfactant and at least one oxidation dye, as well as its uses for dyeing, for dyeing keratinous fibres, in particular human hair.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in U.S. Pat. No. 3,251,742, Patent Applications FR-A-2,112,549, FR-A-2,694,018, EP-A-0, 504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The applicant has surprisingly discovered novel compositions containing, as oxidizing system, at least one enzyme of the laccase type and at least one particular anionic surfactant which will be defined in greater detail below, capable of constituting, in the presence of oxidation dye(s) (oxidation dye precursors and/or couplers), ready-to-use dyeing formulations giving colours which are more homogeneous, more intense and more chromatic without causing significant degradation or decolouring of the keratinous fibres, which exhibit low selectivity and good resistance to various attacks to which the hair may be subjected.

These discoveries form the basis of the present invention.

The first subject of the present invention is therefore a ready-to-use composition intended for dyeing keratinous fibres, in particular human keratinous fibres and more particularly human hair, comprising, in a carrier appropriate for keratinous fibres:

(a) at least one enzyme of the laccase type;
(b) at least one anionic surfactant chosen from the group consisting of:
   (i) acyl isethionates;
   (ii) acyl taurates;
   (iii) sulphosuccinates of the following formula (I):

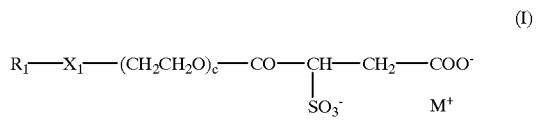

in which $X_1$ denotes an oxygen atom, the —CONH radical, the radical

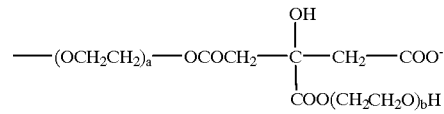

and c=0 to 10 with 1<a+b+c<10,

M denoting H, ammonium, Na or K or an organic amine residue, $R_1$ denoting a saturated or unsaturated, linear or branched $C_{12}$–$C_{30}$ aliphatic group, it being understood that if $X_1$ denotes oxygen, c=0;

(iv) acyl sarcosinates of the following formula (II):

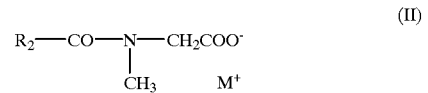

in which $R_2$ denotes a saturated or unsaturated, linear or branched $C_{12}$–$C_{30}$ aliphatic group, M having the same meaning as defined above;

(v) acyl glutamates of the following formula (III):

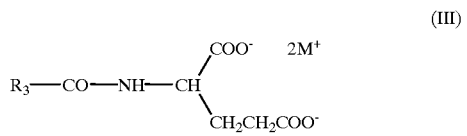

in which $R_3$ denotes a saturated or unsaturated, linear or branched $C_8$–$C_{30}$ aliphatic group, M having the same meaning as defined above;

(vi) polyoxyalkylenated ether carboxylic acids and their salts;
(vii) fatty glucamide sulphates;
(viii) alkyl galactoside uronates;
(ix) anionic derivatives of alkyl polyglucoside;
(x) mixtures thereof;
(c) at least one oxidation dye.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense*, in the extracts of Podocarpaceae, Rosmarinus off., *Solanum tuberosum,* Iris sp., Coffea sp., *Daucus carrota, Vinca minor, Persea americana, Catharenthus roseus,* Musa sp., *Malus pumila, Gingko biloba, Monotropa hypopithys* (Indian pipe), Aesculus sp., *Acer pseudoplatanus, Prunus persica, Pistacia palaestina.*

Among the laccases of fungal origin optionally obtained by biotechnology which can be used according to the invention, there may be mentioned the laccase(s) derived from *Polyporus versicolor, Rhizoctonia practicola* and *Rhus vernicifera* as indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae,* or variants thereof. There may also be mentioned those derived from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The ulac unit corresponds to the quantity of enzyme catalysing the conversion of 1 mmol of syringaldazine per minute at pH 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in ulac units.

The quantities of laccase used in the compositions of the invention will vary according to the nature of the laccase chosen. Preferably, they will vary from 0.5 to 2000 ulac, or from 1000 to $4 \times 10^7$ u units, or from 20 to $2 \times 10^6$ ulac units per 100 g of composition.

The preferred acyl isethionates and acyl taurates in accordance with the invention correspond to the following general structure:

$$R-CH_2-CH_2-SO_3^{-M+} \qquad (IV)$$

where R denotes an R'COO group or an R'CONR" group with R' denoting a saturated or unsaturated, linear or branched $C_8-C_{30}$ aliphatic group and R" denoting hydrogen or a $C_1-C_4$ alkyl radical and M denoting H, ammonium, Na or K or an organic amine, in particular alkanolamine, residue.

Among the sulphosuccinates of formula (I) according to the present invention, there may be mentioned disodium lauramido MEA sulphosuccinate, disodium lauramido PEG2 sulphosuccinate, disodium PEG5 laurylcitrate sulphosuccinate.

The polyoxyalkylenated ether carboxylic acids and their salts in accordance with the invention are preferably those comprising from 2 to 50 ethylene oxide groups, and mixtures thereof. The anionic surfactants of the polyoxyalkylenated ether carboxylic acid or salt type are in particular those which correspond to the following formula (V):

$$R_4-(OC_2H_4)_n-OCH_2COOA \qquad (V)$$

in which:
$R_4$ denotes an alkyl or alkylaryl group, and n is an integer or a decimal number (mean value) which may vary from 2 to 24 and preferably from 3 to 10, the alkyl radical having between 6 and 20 carbon atoms approximately, and aryl preferably denoting phenyl, A denotes H, ammonium, Na, K, Li, Mg or a monoethanolamine or triethanolamine residue. It is also possible to use mixtures of compounds of formula (V), in particular mixtures in which the $R_4$ groups are different.

Compounds of formula (V) are sold for example by the company KAO under the names AKYPOS (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, RO 50) or by the company SANDOZ under the names SANDOPAN (DTC Acid, DTC).

The fatty glucamide sulphates which may be used according to the invention are those described in patent application DE 44 43 645 whose content forms an integral part of the description.

The alkyl galactoside uronates which can be used according to the invention are those described in patent EP-B-0, 701,430 whose content forms an integral part of the description.

The anionic derivatives of alkyl polyglycoside are preferably chosen from
alkyl polyglucoside sulphates or sulphonates, or mixtures thereof;
alkyl polyglucoside ether carboxylates;
alkyl polyglucoside sulphosuccinates;
alkyl polyglucoside isethionates;
alkyl polyglucoside phosphates.

These anionic derivatives of alkyl polyglucoside are in particular described in patents DE 39 18 135, DE 40 21 760, DE 42 39 390, DE 43 36 803, DE 43 37 035 and U.S. Pat. No. 5,001,114.

According to the present invention, the use of the following anionic surfactants is preferred:
acyl isethionates;
polyoxyalkylenated ether carboxylic acids and their salts;
anionic derivatives of alkyl polyglucoside.

The dyeing compositions in accordance with the invention contain the particular anionic surfactants defined above in contents by weight which may be between 0.1% and 20%, preferably between 0.5% and 15% and still more preferably between 1% and 10%, relative to the total weight of the composition.

The nature of the oxidation base(s) and/or of the couplers used in the ready-to-use dyeing composition is not critical.

The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (V) and their addition salts with an acid:

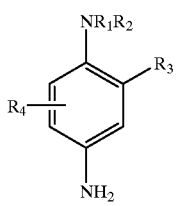

(VI)

in which:
R$_1$ represents a hydrogen atom, a C$_1$–C$_4$ alkyl radical, a monohydroxy(C$_1$–C$_4$ alkyl) radical, a polyhydroxy (C$_2$–C$_4$ alkyl) radical, a (C$_1$–C$_4$) alkoxy (C$_1$–C$_4$) alkyl radical, a C$_1$–C$_4$ alkyl radical substituted with a nitrogen-containing group, a phenyl radical or a 4'-aminophenyl radical;
R$_2$ represents a hydrogen atom, a C$_1$–C$_4$ alkyl radical, a monohydroxy(C$_1$–C$_4$ alkyl) radical, a polyhydroxy (C$_2$–C$_4$ alkyl) radical, a (C$_1$–C$_4$) alkoxy (C$_1$–C$_4$) alkyl radical or a C$_1$–C$_4$ alkyl radical substituted with a nitrogen-containing group;
R$_3$ represents a hydrogen atom, a halogen atom such as a chlorine, bromine, iodine or fluorine atom, a C$_1$–C$_4$ alkyl radical, a monohydroxy(C$_1$–C$_4$ alkyl) radical, a hydroxy(C$_1$–C$_4$ alkoxy) radical, an acetylamino(C$_1$–C$_4$ alkoxy) radical, a mesylamino(C$_1$–C$_4$ alkoxy) radical or a carbamoylamino(C$_1$–C$_4$ alkoxy) radical,
R$_4$ represents a hydrogen or halogen atom or a C$_1$–C$_4$ alkyl radical.

Among the nitrogen-containing groups of formula (VI) above, there may be mentioned in particular the amino, mono(C$_1$–C$_4$)alkylamino, (C$_1$–C$_4$) dialkylamino, (C$_1$–C$_4$) trialkylamino, monohydroxy(C$_1$–C$_4$)alkylamino, imidazolinium and ammonium radicals.

Among the para-phenylenediamines of formula (VI) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phehylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamiine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (VI) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (VII), and their addition salts with an acid:

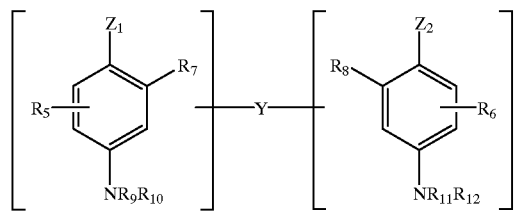

(VII)

in which:
Z$_1$ and Z$_2$, which are identical or different, represent a hydroxyl or —NH$_2$ radical which may be substituted with a C$_1$–C$_4$ alkyl radical or with a linking arm Y;
the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or C$_1$–C$_6$ alkoxy radicals;
R$_5$ and R$_6$ represent a hydrogen or halogen atom, a C$_1$–C$_4$ alkyl radical, a monohydroxy(C$_1$–C$_4$ alkyl) radical, a polyhydroxy(C$_2$–C$_4$ alkyl) radical, an amino(C$_1$–C$_4$ alkyl) radical or a linking arm Y;
R$_7$, R$_8$, R$_9$, R$_{10}$, R$_{11}$ and R$_{12}$, which are identical or different, represent a hydrogen atom, a linking arm Y or a C$_1$–C$_4$ alkyl radical;

it being understood that the compounds of formula (VII) contain only one linking arm Y per molecule.

Among the nitrogen-containing groups of formula (VII) above, there may be mentioned in particular the amino, mono($C_1$–$C_4$)alkylamino, ($C_1$–$C_4$) dialkylamino, ($C_1$–$C_4$) trialkylamino, monohydroxy($C_1$–$C_4$)alkylamino, imidazolinium and ammonium radicals.

Among the double bases of formulae (VII) above, there may be mentioned more particularly N,N'-bis($^b$-hydroxyethyl)-N,N'-bis(4'-aminophenyl)-1,3-diaminopropanol, N,N'-bis($^b$-hydroxyethyl)-N,N'-bis(4'-aminophenyl)ethylenediamine, N,N'-bis(4-aminophenyl)tetramethylenediamine, N,N'-bis($^b$-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (VII), N,N'-bis($^b$-hydroxyethyl)-N,N'-bis(4'-aminophenyl)-1,3-diaminopropanol, 1,8-bis(2,5-diaminophenoxy)- 3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (VIII), and their addition salts with an acid:

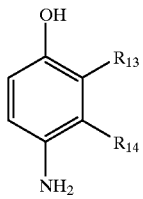

in which:
  $R_{13}$ represents a hydrogen or halogen atom, a $C_1$–$C_4$ alkyl, monohydroxy ($C_1$–$C_4$ alkyl), ($C_1$–$C_4$) alkoxy ($C_1$–$C_4$)alkyl, amino ($C_1$–$C_4$ alkyl) or hydroxy($C_1$–$C_4$) alkylamino($C_1$–$C_4$ alkyl) radical,
  $R_{14}$ represents a hydrogen or halogen atom, a $C_1$–$C_4$ alkyl, monohydroxy($C_1$–$C_4$ alkyl), polyhydroxy ($C_2$–$C_4$ alkyl), amino($C_1$–$C_4$ alkyl), cyano($C_1$–$C_4$ alkyl) or ($C_1$–$C_4$)alkoxy($C_1$–$C_4$) alkyl radical,
it being understood that at least one of the radicals $R_{13}$ or $R_{14}$ represents a hydrogen atom.

Among the para-aminophenols of formula (VIII) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol; 4-amino-2-aminomethylphenol, 4-amino-2-($^b$-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-($^b$-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-($^b$-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triamninopyrazole, 3,5-diamino-1-methyl-4-methylaminopyrazole, 3,5-diamino-4-($^b$-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (IX), their addition salts with an acid or with a base and their tautomeric forms, when a tautomeric equilibrium exists:

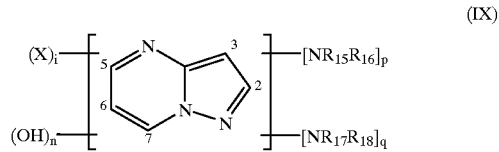

in which:
  $R_{15}$, $R_{16}$, $R_{17}$ and $R_{18}$, which are identical or different, denote a hydrogen atom, a $C_1$–$C_4$,alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$ alkyl) radical, a $C_1$–$C_4$ aminoalkyl radical (it being possible for the amine to be protected with an acetyl, ureido or sulphonyl radical), a ($C_1$–$C_4$)alkylamino($C_1$–$C_4$ alkyl) radical, a di-[($C_1$–$C_4$)alkyl]amino($C_1$–$C_4$ alkyl) radical (it being possible for the dialkyl radicals to form a carbon-containing ring or a 5- or 6-membered heterocycle), a hydroxy($C_1$–$C_4$)alkyl- or di-[hydroxy ($C_1$–$C_4$)alkyl]amino ($C_1$–$C_4$ alkyl) radical, the X radicals, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$) alkylamino ($C_1$–$C_4$ alkyl) radical, a di-[($C_1$–$C_4$) alkyl] amino($C_1$–$C_4$ alkyl) radical (it being possible for the dialkyls to form a carbon-containing ring or a 5- or 6-membered heterocycle), a hydroxy($C_1$–$C_4$)alkyl or di-[hydroxy($C_1$–$C_4$)alkyl]amino($C_1$–$C_4$ alkyl) radical, an amino radical, a ($C_1$–$C_4$)alkyl- or di-[($C_1$–$C_4$)alkyl]-amino radical; a halogen atom, a carboxylic acid group, a sulphonic acid group;

i equals 0, 1, 2 or 3;
p equals 0 or 1;
q equals 0 or 1;
n equals 0 or 1;
with the proviso that:
the sum p+q is different from 0;
when p+q is equal to 2, then n equals 0 and the groups $NR_{15}R_{16}$ and $NR_{17}R_{18}$ occupy positions (2,3); (5,6); (6,7); (3,5) or (3,7);
when p+q is equal to 1, then n equals 1 and the group $NR_{15}R_{16}$ (or $NR_{17}R_{18}$) and the OH group occupy positions (2,3); (5,6); (6,7); (3,5) or (3,7).

When the pyrazolo[1,5-a]pyrimidines of formula (IX) above are such that they comprise a hydroxyl group on one of the positions 2, 5 or 7 at the a position with respect to a nitrogen atom, a tautomeric equilibrium exists which is represented for example by the following scheme:

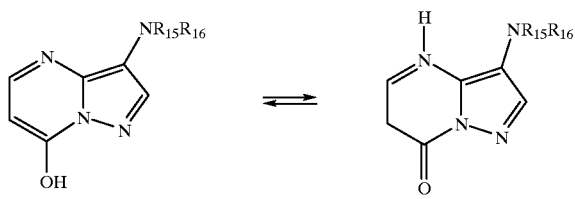

Among the pyrazolo[1,5-a]pyrimidines of formula (IX) above, there may be mentioned in particular:
pyrazolo[1,5-a]pyrimidine-3,7-diamine;.
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl) (2-hydroxyethyl)amino]ethanol;
2-[(7-aminopyrazolo[1,5-a]pyrimidin-3-yl)(2-hydroxyethyl)amino]ethanol,
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and their addition salts and their tautomeric forms, when a tautomeric equilibrium exists.

The pyrazolo[1,5-a]pyrimidines of formula (IX) above may be prepared by cyclization from an aminopyrazole according to the syntheses described in the following references:

EP 628559 BEIERSDORF-LILLY
R. Vishdu, H. Navedul, Indian J. Chem., 34b(6), 514, 1995.

N. S. Ibrahim, K. U. Sadek, F. A. Abdel-Al, Arch. Pharm., 320, 240, 1987.

R. H. Springer, M. B. Scholten, D. E. O'Brien, T. Novinson, J. P. Miller, R. K. Robins, J. Med. Chem., 25, 235, 1982.

T. Novinson, R. K. Robins, T. R. Matthews, J. Med. Chem., 20, 296, 1977.

U.S. Pat. No. 3907799 ICN PHARMACEUTICALS

The pyrazolo[1,5-a]pyrimidines of formula (IX) above can also be prepared by cyclization from hydrazine according to the syntheses described in the following references:

A. McKillop and R. J. Kobilecki, Heterocycles, 6(9), 1355, 1977.

E. Alcade, J. De Mendoza, J. M. Marcia-Marquina, C. Almera, J. Elguero, J. Heterocyclic Chem., 11(3), 423, 1974.

K. Saito, I. Hori, M. Higarashi, H. Midorikawa, Bull. Chem. Soc. Japan, 47(2), 476, 1974.

The oxidation base(s) in accordance with the invention preferably represent from 0.0005 to 12% by weight approximately of the total weight of the ready-to-use dyeing composition, and still more preferably from 0.005 to 6% by weight approximately of this weight.

The coupler(s) which can be used in the ready-to-use dyeing composition in accordance with the invention are those conventionally used in oxidation dyeing compositions, that is to say meta-phenylenediamines, meta-aminophenols and meta-diphenols, the mono- or polyhydroxylated derivatives of naphthalene, sesamol and its derivatives and heterocyclic compounds such as for example indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, 3,5-pyrazolinedione derivatives, pyrrolo[3,2-d]oxazole derivatives, pyrazolo[3,4-d]thiazole derivatives, thiazoloazole S-oxide derivatives, thiazoloazole S,S-dioxide derivatives, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The dyeing composition of the invention may also contain, in addition to the oxidation dyes defined above, direct dyes in order to increase the shimmer of the shades. These direct dyes can in particular then be chosen from nitro, azo or anthraquinone dyes.

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye as defined above and, on the other hand, a composition (B) containing, in a medium appropriate for dyeing, at least one enzyme of the laccase type and at least at least one particular anionic surfactant as defined above, and then in mixing them at the time of use before applying this mixture to the keratinous fibres. According to a specific embodiment of the invention, the anionic surfactant as defined above can be incorporated into the composition (A).

Another subject of the invention is a multi-compartment device or dyeing (kit) or any other multi-compartment packaging system in which a first compartment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The medium appropriate for keratinous fibres (or carrier) of the ready-to-use dyeing compositions for keratinous fibres in accordance with the invention generally consists of water or of a mixture of water and of at least one organic solvent in order to solubilize the compounds which might not be sufficiently soluble in water. As organic solvent, there may be mentioned for example $C_1$–$C_4$ alkanols such as ethanol and isopropanol as well as aromatic alcohols such as benzyl alcohol, similar products and mixtures thereof.

The solvents may be present in proportions preferably of between 1 and 40% by weight approximately relative to the total weight of the dyeing composition, and still more preferably between 5 and 30% by weight approximately.

The pH of the ready-to-use dyeing compositions for keratinous fibres in accordance with the invention is chosen such that the enzymatic activity of the laccase is not impaired. It generally varies from 4 to 11 approximately, and more preferably from 6 to 9 approximately.

The ready-to-use dyeing compositions for keratinous fibres in accordance with the invention may also contain various adjuvants conventionally used in dyeing compositions, such as anionic surfactants other than those used in accordance with the present invention, cationic, nonionic, amphoteric or zwitterionic surfactants or mixtures thereof, polymers, thickeners, antioxidants, enzymes different from the laccases used in accordance with the invention, such as for example peroxidases or oxidoreductases containing 2 electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the compositions in accordance with the invention are not, or substantially not, impaired by the addition(s) envisaged.

The ready-to-use dyeing compositions for keratinous fibres in accordance with the invention can be provided in various forms, such as in the form of liquids, creams, gels, optionally pressurized, or in any other form appropriate for dyeing keratinous fibres, in particular human hair.

In the ready-to-use dyeing compositions of the invention, the oxidation dye(s) and the laccase(s) are present in the said composition which should be free of gaseous oxygen, so as to avoid any premature oxidation of the oxidation dye(s).

Concrete examples illustrating the invention will now be given.

In the text which follows or in the preceding text, unless otherwise stated, the percentages are expressed by weight.

The following examples illustrate the invention with no limitation being implied.

DYEING EXAMPLES 1 to 3

The following ready-to-use dyeing compositions were prepared (contents in grams):

| COMPOSITION | 1 | 2 | 3 |
|---|---|---|---|
| Laccase obtained from Rhus vernicifera containing 180 units/mg sold by the company SIGMA | 1.8 | 1.8 | 1.8 |
| para-Phenylenediamine | 0.254 | 0.254 | 0.254 |
| 2,4-Diaminophenoxyethanol.2HCl | 0.260 | 0.260 | 0.260 |
| Ethanol | 20.000 | 20.000 | 20.000 |
| Triethanolainine cocoyl glutamate in aqueous solution containing 30% of active substance (AS) sold under the name ACYLGLUTAMATE CT12 by the company AJINOMOTO | 4.500 (AS) | X | X |
| Powdered cocoyl isethionate sold under the name JORDAPON CI POWDER by the company PPG | X | 5.000 | X |
| Lauryl ether carboxylic acid containing 10 mol of ethylene oxide sold under the name AKYPO RLM 100 by the company KAO | X | X | 5.000 |
| pH agent qs pH | 6.5 | 6.5 | 6.5 |
| Demineralized water qs | 100 | 100 | 100 |

The ready-to-use dyeing compositions described above were applied at the temperature of 30° C. to locks of natural grey hair which is 90% white for 40 minutes. The hair was then rinsed, washed with a standard shampoo and then dried. The hair had a bluish-grey colour in the three cases.

In the examples described above, 1.8% of Rhus vernicifera laccase at 180 units/mg can be replaced by 1% of Pyricularia Orizae laccase at 100 units/mg sold by the company I.C.N.

What is claimed is:

1. A composition for dyeing keratinous fibers, comprising:

(a) at least one enzyme of the laccase type;
   (b) at least one anionic surfactant chosen from:
      (i) acyl isethionates;
      (ii) acyl taurates;

(iii) sulphosuccinates of the formula (I):

$$R_1-X_1-(CH_2CH_2O)_c-CO-\underset{\underset{M^+}{SO_3^-}}{CH}-CH_2-COO^-$$ (I)

in which
X$_1$ is chosen from an oxygen atom, the —CONH group, and $$-(OCH_2CH_2)_a-OCOCH_2-\underset{\underset{COO(CH_2CH_2O)_bH}{\overset{OH}{|}}}{C}-CH_2-COO^-$$

groups and c=0 to 10 with 1<a+b+c<10, wherein if X$_1$ is an oxygen atom, then c=0, M is chosen from a hydrogen atom, ammonia, Na, K, and an organic amine residue, R$_1$ is chosen from saturated and unsaturated, linear and branched C$_{12}$–C$_{30}$ aliphatic groups, optionally substituted;

(iv) acyl sarcosinates of the formula (II):

$$R_2-CO-\underset{\underset{M^+}{CH_3}}{N}-CH_2COO^-$$ (II)

in which
R$_2$ is chosen from saturated and unsaturated, linear and branched C$_{12}$–C$_{30}$ aliphatic groups, optionally substituted, M is chosen from a hydrogen atom, ammonia, Na, K, and an organic amine residue;

(v) acyl glutamates of the formula (III):

$$R_3-CO-NH-CH\overset{COO^-\quad 2M^+}{\underset{CH_2CH_2COO^-}{\diagdown}}$$ (III)

in which
R$_3$ is chosen from saturated and unsaturated, linear and branched C$_8$–C$_{30}$ aliphatic groups, optionally substituted, M is chosen from a hydrogen atom, ammonia, Na, K, and an organic amine residue;

(vi) polyoxyalkylenated ether carboxylic acids and their salts;

(vii) fatty glucamide sulphates;

(viii) alkyl galactoside uronates; and (ix) anionic derivatives of alkyl polyglucoside; and (c) at least one oxidation dye.

2. A composition according to claim 1, wherein said keratinous fibers are human keratinous fibers.

3. A composition according to claim 2, wherein said human keratinous fibers are hair.

4. A composition according to claim 1, wherein said at least one enzyme of the laccase type is chosen from laccases of plant origin, animal origin, fungal origin, and bacterial origin, and laccases obtained by biotechnology.

5. A composition according to claim 1, wherein said at least one enzyme of the laccase type is chosen from those produced by plants performing chlorophyll synthesis.

6. A composition according to claim 1, wherein said at least one enzyme of the laccase type is chosen from those extracted from plants chosen from Anacardiaceae, Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys*, Aesculus sp., *Acer pseudoplatanus, Prunus persica*, and *Pistacia palaestina*.

7. A composition according to claim 1, wherein said at least one enzyme of the laccase type is chosen from those derived from fungi chosen from *Pyricularia orizae, Polyporus versicolor, Rhizoctonia praticola, Rhus vernicifera, Scytalidium, Polyporus pinsitus, Myceliophtora thermophila, Rhizoctonia solani, Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all of said fungi.

8. A composition according to claim 1, wherein said at least one enzyme of the laccase type is in a quantity ranging from 0.5 to 2000 lacu units per 100 g of said composition.

9. A composition according to claim 1, wherein said at least one enzyme of the laccase type is in a quantity ranging from 20 to $2 \times 10^6$ ulac units per 100 g of said composition.

10. A composition according to claim 1, wherein said at least one enzyme of the laccase type is in a quantity ranging from 1000 to $4 \times 10^7$ u units per 100 g of said composition.

11. A composition according to claim 1, wherein said at least one anionic surfactant is chosen from:
   acyl isethionates;
   polyoxyalkylenated ether carboxylic acids and their salts; and
   anionic derivatives of alkyl polyglucoside.

12. A composition according to claim 1, wherein said acyl isethionates and acyl taurates are of the formula (IV):

$$R-CH_2-CH_2-SO_3^-M^+ \quad (IV)$$

in which
   R is chosen from R'COO groups and R'CONR" groups with R' being chosen from saturated and unsaturated, linear and branched C$_8$–C$_{30}$ aliphatic groups, optionally substituted, and R" being chosen from a hydrogen atom and C$_1$–C$_4$ alkyl groups, and M is chosen from a hydrogen atom, ammonia, Na, K, and an organic amine residue.

13. A composition according to claim 1, wherein said polyoxyalkylenated ether carboxylic acids and their salts comprise from 2 to 50 ethylene oxide groups.

14. A composition according to claim 1, wherein said polyoxyalkylenated ether carboxylic acids and their salts are of the formula (V):

$$R_4-(OC_2H_4)_n-OCH_2COOA \quad (V)$$

in which:
   R$_4$ is chosen from alkyl groups and alkylaryl groups, wherein said alkyl groups and said alkyl portion of said alkylaryl groups comprise from about 6 to about 20 carbon atoms, n is chosen from an integer and a decimal number (mean value), which ranges from 2 to 24, A is chosen from a hydrogen atom, ammonium, Na$^+$, K$^+$, Li$^+$, Mg$^{2+}$, a monoethanolamine cationic residue and a triethanolamine cationic residue.

15. A composition according to claim 14, wherein said polyoxyalkylenated ether carboxylic acid salts are of the formula

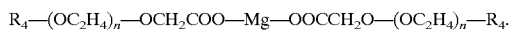

16. A composition according to claim 14, wherein said n is chosen from an integer and a decimal number (mean value), which ranges from 3 to 10.

17. A composition according to claim 14, wherein said aryl portion of said alkylaryl groups is phenyl.

18. A composition according to claim 1, wherein said anionic derivatives of alkyl polyglucoside are chosen from
    alkyl polyglucoside sulphates;
    alkyl polyglucoside sulphonates;
    alkyl polyglucoside ether carboxylates;
    alkyl polyglucoside sulphosuccinates;
    alkyl polyglucoside isethionates; and
    alkyl polyglucoside phosphates.

19. A composition according to claim 1, wherein said at least one anionic surfactant is in a concentration ranging from about 0.1% to about 20% by weight relative to the total weight of the composition.

20. A composition according to claim 19, wherein said at least one anionic surfactant is in a concentration ranging from about 0.5% to about 15% by weight relative to the total weight of the composition.

21. A composition according to claim 1, wherein said at least one oxidation dye is chosen from at least one oxidation base and at least one coupler.

22. A composition according to claim 21, wherein said at least one oxidation base is chosen from ortho- and para-phenylenediamines, bisphenylalkylenediamines, ortho- and para-aminophenols, heterocyclic bases, and the acid addition salts of all of said at least one oxidation bases.

23. A composition according claim 22, wherein said acid addition salts of the oxidation bases are chosen from hydrochlorides, hydrobromides, sulphates, tartrates, lactates and acetates.

24. A composition according to claim 21, wherein said at least one oxidation base is present in a concentration ranging from 0.0005% to 12% by weight relative to the total weight of the composition.

25. A composition according to claim 21, wherein said at least one coupler is chosen from meta-phenylenediamines, meta-aminophenols, metadiphenols, heterocyclic couplers, and the acid addition salts of all of said at least one couples.

26. A composition according claim 25, wherein said acid addition salts of the couplers are chosen from hydrochlorides, hydrobromides, sulphates, tartrates, lactates and acetates.

27. A composition according to claim 21, wherein said at least one coupler is present in a concentration ranging from 0.0001% to 10% by weight relative to the total weight of the composition.

28. A composition according to claim 1, further comprising at least one direct dye.

29. A composition according to claim 1, further comprising at least one carrier appropriate for the keratinous fibers.

30. A composition according to claim 29, wherein said carrier comprises a substance chosen from water and at least one organic solvent.

31. A composition according to claim 30, wherein said at least one organic solvent is present in a concentration ranging from 1% to 40% by weight relative to the total weight of the composition.

32. A composition according to claim 31, wherein said at least one organic solvent is present in a concentration ranging from 5% to 30% by weight relative to the total weight of the composition.

33. A composition according to claim 1, wherein the pH ranges from about 4 to about 11.

34. A composition according to claim 33, wherein the pH ranges from about 6 to about 9.

35. A composition according to claim 1, further comprising at least one suitable cosmetic adjuvant chosen from anionic surfactants different from said at least one anionic surfactant as defined in claim 1, polymers, antioxidants, enzymes different from said at least one enzyme of the laccase type as defined in claim 1, penetrating agents, sequestering agents,
    perfumes, buffers, dispersing agents, film-forming agents, screening agents, vitamins, preservatives and opacifying agents.

36. A method of dyeing keratinous fibers, comprising applying to said keratinous fibers for a sufficient time to develop a desired color at least one dyeing composition comprising:
    (a) at least one enzyme of the laccase type;
    (b) at least one anionic surfactant chosen from:
        (i) acyl isethionates;
        (ii) acyl taurates;
        (iii) sulphosuccinates of the formula (I):

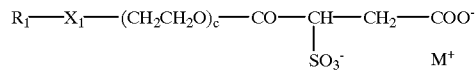

in which
    $X_1$ is chosen from an oxygen atom, the —CONH group, and

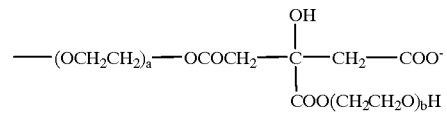

groups and c=0 to 10 with 1<a+b+c<10, wherein if $X_1$ is an oxygen atom, then c=0, M is chosen from a hydrogen atom, ammonia, Na, K, and an organic amine residue, $R_1$ is chosen from saturated and unsaturated, linear and branched $C_{12}$–$C_{30}$ aliphatic groups, optionally substituted;

(iv) acyl sarcosinates of the formula (II):

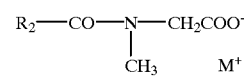

in which
    $R_2$ is chosen from saturated and unsaturated, linear and branched $C_{12}$–$C_{30}$ aliphatic groups, optionally substituted,
    M is chosen from a hydrogen atom, ammonia, Na, K, and an organic amine residue;

(v) acyl glutamates of the formula (III):

$$R_3-CO-NH-CH\begin{smallmatrix}COO^-\\ \\CH_2CH_2COO^-\end{smallmatrix}\quad 2M^+ \qquad (III)$$

in which
- $R_3$ is chosen from saturated and unsaturated, linear and branched $C_8$–$C_{30}$ aliphatic groups, optionally substituted,
- M is chosen from a hydrogen atom, ammonia, Na, K, and an organic amine residue;

(vi) polyoxyalkylenated ether carboxylic acids and their salts;
(vii) fatty glucamide sulphates;
(viii) alkyl galactoside uronates; and
(ix) anionic derivatives of alkyl polyglucoside; and (c) at least one oxidation dye.

37. A method of dyeing keratinous fibers according to claim 36, wherein said keratinous fibers are human keratinous fibers.

38. A method of dyeing keratinous fibers according to claim 37, wherein said human keratinous fibers are hair.

39. A method of dyeing keratinous fibers, comprising the steps of
(a) storing a first composition,
(b) storing a second composition separately from said first composition,
(c) mixing the first composition with the second composition to form a mixture, and
(d) applying said mixture to said keratinous fibers for a time sufficient to achieve a desired coloration;
wherein said first composition comprises, in a medium appropriate for dyeing, at least one oxidation dye,
wherein said second composition comprises, in a medium appropriate for keratinous fibers, at least one enzyme of the laccase type, and
further wherein at least one of said first composition and said second composition comprises at least one anionic surfactant chosen from:
(i) acyl isethionates;
(ii) acyl taurates;
(iii) sulphosuccinates of the formula (I):

$$R_1-X_1-(CH_2CH_2O)_c-CO-\underset{SO_3^-}{\overset{}{CH}}-CH_2-COO^- \quad M^+ \qquad (I)$$

in which
X$_1$ is chosen from an oxygen atom, the —CONH group, and $$-(OCH_2CH_2)_a-OCOCH_2-\underset{COO(CH_2CH_2O)_bH}{\overset{OH}{C}}-CH_2-COO^-$$

groups and c=0 to 10 with 1<a+b+c<10, wherein if $X_1$ is an oxygen atom, then c=0,
M is chosen from a hydrogen atom, ammonia, Na, K, and an organic amine residue, $R_1$ is chosen from saturated and unsaturated, linear and branched $C_{12}$–$C_{30}$ aliphatic groups, optionally substituted;

(iv) acyl sarcosinates of the formula (1l):

$$R_2-CO-\underset{CH_3}{\overset{}{N}}-CH_2COO^- \quad M^+ \qquad (II)$$

in which
$R_2$ is chosen from saturated and unsaturated, linear and branched $C_{12}$–$C_{30}$ aliphatic groups, optionally substituted,
M is chosen from a hydrogen atom, ammonia, Na, K, and an organic amine residue;

(v) acyl glutamates of the formula (III):

$$R_3-CO-NH-CH\begin{smallmatrix}COO^-\\ \\CH_2CH_2COO^-\end{smallmatrix}\quad 2M+ \qquad (III)$$

in which
$R_3$ is chosen from saturated and unsaturated, linear and branched $C_8$–$C_{30}$ aliphatic groups, optionally substituted,
M is chosen from a hydrogen atom, ammonia, Na, K, and an organic amine residue;

(vi) polyoxyalkylenated ether carboxylic acids and their salts;
(vii) fatty glucamide sulphates;
(viii) alkyl galactoside uronates; and
(ix) anionic derivatives of alkyl polyglucoside.

40. A multicompartment device or a dyeing kit, comprising a first compartment containing a composition (A) comprising, in a medium appropriate for dyeing, at least one oxidation dye and a second compartment containing a composition (B) comprising, in a medium appropriate for keratinous fibers, at least one enzyme of the laccase type, wherein at least one of said composition (A) and said composition (B) comprises at least one anionic surfactant chosen from:
(i) acyl isethionates;
(ii) acyl taurates;
(iii) sulphosuccinates of the formula (I):

$$R_1-X_1-(CH_2CH_2O)_c-CO-\underset{SO_3^-}{\overset{}{CH}}-CH_2-COO^- \quad M^+ \qquad (I)$$

in which
$X_1$ is chosen from an oxygen atom, the —CONH group, and $$-(OCH_2CH_2)_a-OCOCH_2-\underset{COO(CH_2CH_2O)_bH}{\overset{OH}{C}}-CH_2-COO^-$$

groups and c=0 to 10 with 1<a+b+c<10, wherein if $X_1$ is an oxygen atom, then c=0, M is chosen from a hydrogen atom, ammonia, Na, K, and an organic amine residue, $R_1$ is chosen from saturated and unsaturated, linear and branched $C_{12}$–$C_{30}$ aliphatic groups, optionally substituted;

iv) acyl sarcosinates of the formula (II):

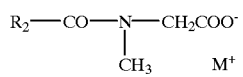

(II)

in which $R_2$ is chosen from saturated and unsaturated, linear and branched $C_{12}$–$C_{30}$ aliphatic groups, optionally substituted, M is chosen from a hydrogen atom, ammonia, Na, K, and an organic amine residue;

(v) acyl glutamates of the formula (III):

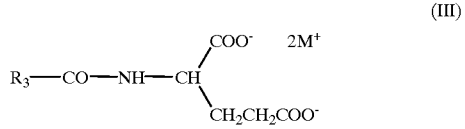

(III)

in which $R_3$ is chosen from saturated and unsaturated, linear and branched $C_8$–$C_{30}$ aliphatic groups, optionally substituted, M is chosen from a hydrogen atom, ammonia, Na, K, and an organic amine residue;

(vi) polyoxyalkylenated ether carboxylic acids and their salts;

(vii) fatty glucamide sulphates;

(viii) alkyl galactoside uronates; and (ix) anionic derivatives of alkyl polyglucoside.

* * * * *

UNITED STATES PATENT AND TRADEMARK OFFICE
CERTIFICATE OF CORRECTION

PATENT NO. : 6,383,231 B1
DATED : May 7, 2002
INVENTOR(S) : Gérard Lang et al.

It is certified that error appears in the above-identified patent and that said Letters Patent is hereby corrected as shown below:

Column 13,
Line 39, "formula (I11)" should read -- formula (III) --.

Column 15,
Lines 3-6, please change:
"A is chosen from a hydrogen atom, ammonium, $Na^+$, $K^+$,
    $Li^+$,
$Mg^{2+}$, a monoethanolamine cationic residue and a trietha-
nolamine cationic residue."
to:
-- A is chosen from a hydrogen atom, ammonium, $Na^+$, $K^+$, $Li^+$, $Mg^{2+}$, a
    monoethanolamine cationic residue and a triethanolamine cationic residue. --
Line 41, after "according" insert -- to --.
Line 52, "couples" should read -- couplers --.
Line 53, after "according" insert -- to --.

Column 17,
Line 12, "C8-$C_{30}$" should read -- $C_8$-$C_{30}$ --.

Column 18,
Line 4, "formula (11)" should read -- formula (II) --.

Signed and Sealed this

Eighth Day of October, 2002

Attest:

JAMES E. ROGAN
Attesting Officer    Director of the United States Patent and Trademark Office